United States Patent [19]
Gronowitz et al.

[11] Patent Number: 6,132,995
[45] Date of Patent: Oct. 17, 2000

[54] METHOD FOR DETERMINING ACTIVITY OF REVERSE TRANSCRIPTASE

[75] Inventors: Jan-Simon Gronowitz; Clas Källander, both of Uppsala; Johan Lennerstrand, Bromma, all of Sweden

[73] Assignee: Cavidi Tech AB, Uppsala, Sweden

[21] Appl. No.: 09/051,084

[22] PCT Filed: Aug. 12, 1996

[86] PCT No.: PCT/SE96/00990

§ 371 Date: Apr. 13, 1998

§ 102(e) Date: Apr. 13, 1998

[87] PCT Pub. No.: WO98/06873

PCT Pub. Date: Feb. 19, 1998

[51] Int. Cl.$^7$ .............................. C12Q 1/68; C12P 19/34; C07H 19/00; C07H 21/02; C07H 21/04

[52] U.S. Cl. .......................... 435/91.1; 435/6; 435/91.2; 536/22.1; 536/23.1; 536/25.3; 536/25.32; 536/24.3; 536/24.33

[58] Field of Search .............................. 435/6, 91.1, 91.2; 536/22.1, 23.1, 25.3, 25.32, 24.3, 24.33

[56] References Cited

U.S. PATENT DOCUMENTS

5,503,978  4/1996  Schneider et al. ........................... 435/6

OTHER PUBLICATIONS

Borukhov et al. "Mapping of trypsin cleavage and antibody–binding sites and delineation of a dispensable domain in the beta subunit of *Escherichia coli* RNA polymerase" Journal of Biological Chemistry, vol. 266, No. 35, pp. 23921–23926, Dec. 1991.

Porstmann et al. "A sensitive non–isotopic assay specific for HIV–1 associated reverse transcriptase" Journal of Virological Methods, vol. 31, pp. 181–188, 1991.

J. Lennerstrand, A.S. Rytting, C. Orvell, J.S. Gronowitz, and C.F.R. Kallander, "A Method for Combined Immunoaffinity Purification and Assay of HIV–1 Reverse Transcriptase Activity Useful for Crude Samples"–Analytical Biochemistry 235, 141–152 (1995), Article No. 0106.

*Primary Examiner*—Jezia Riley
*Attorney, Agent, or Firm*—Bacon & Thomas

[57] ABSTRACT

A method for determining the activity of a nucleotide polymerizing enzyme in a sample, and use of the method for determining HIV 1 RT- and Herpes Simplex DNA-polymerase activity. The enzyme is captured by means of a nonoclonal antibody which is immobilized to a solid carrier and is capable of binding the enzyme without detrimentally effecting the enzyme activity. Contaminants and disturbing factors are removed and the nucleotide polymerization starts by the addition of a reaction solution containing a primer/template construct and nucleotides substrate, the reaction conditions being chosen such that they promote permanent association between antibody enzyme- and primer/template constructs. When necessary a nucleotide substrate, primer/template and reaction solution are washed away from the newly synthesized polymer, and the amount of nucleotide which as been incorporated into the polymer is determined, and the activity of the enzyme is determined with the guidance of this determination.

12 Claims, 9 Drawing Sheets

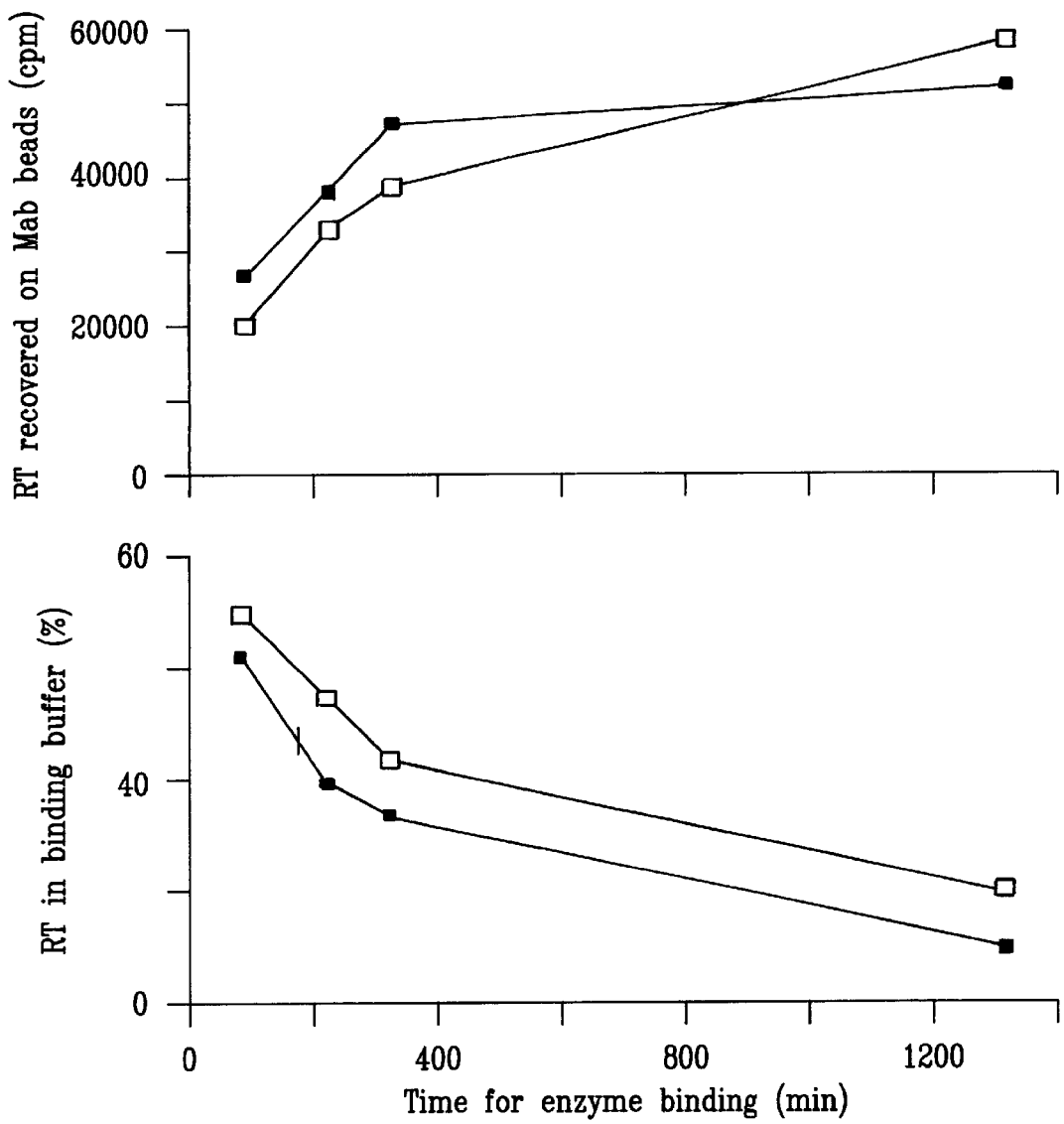

METHOD FOR DETERMINING ACTIVITY OF REVERSE TRANSCRIPTASE

The present invention relates to a method for determining the activity of certain DNA polymerizing enzymes in human or animal body liquids, cell samples or samples from virus infected cultures, these enzymes being caracterized by high processivity. The invention also relates to the use of said method for isoenzyme-typing. The invention also relates to use of said methods for diagnosis and prognosis of tumour deseases or deseases which are caused by or associated with virus infections such as AIDS, T cell leukaemia and herpes virusinfections.

BACKGROUND OF THE INVENTION

Reversed transcriptase, in the following called RT, is a critical enzyme which is responsable for the synthesis of DNA from viral RNA for all retroviruses, including human immune deficiency virus (HIV). Three different enzymatic activities are involved in this process: synthesis of the first DNA strand, degradation of the viral RNA strand in the DNA/RNA hybride and synthesis of the second DNA strand. See e.g. S. P. Goff, (1990) Review, J. AIDS 3, pages 817–831 for an overview.

The RNA and DNA dependent polymerase activities are obviously mediated by the same catalytical group, whereas RNas H activity is mediated through a special part of the molecule. Se e.g. J. Hansen et al. EMBO J. (1988) 7, pages 239–243, M. S. Johnson et al. (1986) PNAS 83, pages 7648–7652. HIV 1 RT appears as a heterodimer in virions consisting of two polypeptides, p66 and p51, with the same N terminals [see e.g. M. M. Lightfoot et al. (1986) J. Virol, 60, pages 771–775, Veronese et al. (1986) Science 231, pages 1289–1291]. p51 is generated by viral protease cleavage of the p66-polypeptides in the dimer of p51 and p15 (see e.g. Mous). In the heterodimer p66 catalyses the polyemerase reaction, but the same sequence in p51 does not [see e.g. Le Grice et al. (1991) EMBO J. 10, pages 3905–3911, Hostomsky et al. (1992), Science 256, pages 1783–1790]. It is assumed that p51 is a part of the binding site for the tRNA primer and a part of the template-primer binding site (see e.g. Kohlstaedt 1992). The RNA-ase H peptid activity in the p66/p51 heterodimer is locatized to the C terminal part of p66 (see e.g. Hansen 1988).

Analysis relating to RT activity has become an accepted technic for detectioning and quantification of retrovirus in cell cultures (see e.g. Pioesz 1980 and Barr-Sinoussi 1983). Together with the p24 antigen test it is used as a confirming test for HIV isolation (see e.g. Jackson 1988, Gupta 1987). RT is also the main target in attempts to find efficient anti-virales against HIV. Many attempts have been made to find selective inhibitors of this enzyme. Although no cure for AIDS not yet has been found, a valuable effect is achieved by treating patients with 3'-azido-3'-deoxy thymidine (AZT). It has, however, been found that treatment with AZT only in a rather short period of treatment (from 3 months to 1 year) produces therapy resistant HIV, with mutated RT. RT tests are presently used for evaluation of reaction mechanisms in potential antivirals. Another great potential use of RT analysis is consequently characterisation of enzymes from therapy resistant mutating viruses.

Conventional measurement of RT activity is carried out with the enzyme in solution, an artificial template/primer construct and tritiated deoxynucleoid triphosphate as the nucleotide substrate (see e.g. Baltimore 1971, Moon & Lee). this system is based on detecting incorporation of radio activity in RNA/DNA hybrids which can be precipitated with trichloro acetic acid (TCA). By using β emitting nucleotides scintillation liquids can be used for detecting radio activity, but this often results in poor reproducability depending on extinction problems. The standard test is coparatibly labor consuming and can not readily be adapted to large scale investigation of a large number of samples. It is also very sensitive to the effects of disturbing factors in the enzyme samples. The latter are often the critical factor for the determination of RT activity in extracts from infected cell cultures or HIV infected individuals. Furthermore, the activity of cellular gammapolymerase enzyme is a potential specificity problem.

During recent years the intensive research relating to HIV has resulted in improvements of RT tests by the use of various techniques.

The incorporation of $^{125}$I labelled substrate resulted in improved sensitivity and eliminated quenching and use of scintillation liquids (Gronowitz et al. 1990). The introduction of templates or primers coupled to solid phases simplified the separation between substrate and product, simplified the need of precipitation with TCA and resulted in a "one tube RT test" (see e.g. Gronowitz 1991, Urabe et al. 1992). Several attempts have also been made to make the test systems less sensitive to disturbing factors.

According to Porstmann et al. 1991 a monoclonal antibody against HIV1-RT is used, which binds to a well in a microplate in order to isolate RT before the analysis. However, this method has been used for determining the RT activity in virus samples which already have been purified by precipitation with PEG and subsequently centrifugation. Furthermore, after immobilization of RT, a complex procedure is used for separating the nucleoside substrate and the soluble labled product. Gronowitz et al. 1991 uses prA/odT bound to a plastic carrier, for affinity purification of HIV-RT in one step directly from cell extracts. The same prA/odT construct is then used as primer/template in the subsequent RT test step.

Recently it has been avoided to use radio activity as a marker in RT analysis by instead using modified nucleotide bases containing antigenic epitopes or structures having av high affinity for defined ligands. The presence of these epitopes or structures in the recently synthesize RNA/DNA hybride is then used for binding antibodies or ligands which have been conjugated with Eg ELISA enzymes. The amount of bound ELISA enzymes has then been determined with a secondary enzym test. Porstmann et al., 1991, makes use of 5-bromo-deoxy-uridine (BrdU) triphosphate as the nucleotide substrate in RT analysis. The amount of incorporated BrdU is determined in a second step with an immune test while using monoclonal anti-BrdU antibodies.

Beery & Scieb, 1992 measures the incorporation of dioxygenine-labled dUTP in newly synthesized DNA instead of radioactively labelled dTTP. In order to be able to separate the non-incorporated nucleotides from newly synthesized DNA also biotine-labelled dUTP is added to the reaction mixture. After reversed transcription the newly synthesized double labelled DNA is immobilized on streptavidine coated ELISA wells and determined photometrical by binding of peroxydase-conjugated anti-digoxygenine antibodies. This method has been the basis for an RT test kit which is available from Boehringer, Mannheim.

Urabe et al. has developed a non-radioactive RT test which is based on the incorporation of biotine-dUTP in an immobilized odT/prA construct. The amount of incorporated nucleotide substrate is measured photometrical after addition of strept-avidine conjugated alkaline phosphatase (AP).

Another commersially used principle for showing RT activity is to use a series of specific sonds for detecting newly synthesized cDNA. This enzymatic reaction makes use of a heteropolymer RNA molecule with a 20 bases oligonucleotide-primer which is complementary with the RNA sequences close to the 5'end. During the RT reaction a complete cDNA strand is produced. After hydrolysis of template-RNa, cDNA is hybridised with two different oligonucleotide sonds, the capture and detection sonds respectively. The capture sond is used for binding cDNA to wells in a microplate. The detection sonds is conjugated to horeradish peroxidase, which results in a colour reaction after washing for removing unused nucleotide substrates and free sonds.

One purpose of the present invention is to provide a method for quantitative determination of certain polymerase activities which removes most of drawbacks of the previously known methods. Another purpose is to provide a kit for specific determination of different polymerase activities. The invention also relates to the use of said methods and products for novel purposes.

These and other objects of the invention, and how they are achieved, will be explained and illustrated in further detail in the subsequent description and the working examples.

The invention is especially illustrated in connection with determination of HIV1 RT- and Herpes Simplex DNA-polymerase activity, but it can also be used in all highly processive polymerases such as retro RT, DNA virus polymerases, cellular gamma- and delta-polymerases and the like.

SUMMARY OF THE INVENTION

One purpose of the present invention is to provide methods, means and devices for diagnosis and supervision of certain diseases which are related to retrovirus infections.

Another object of the invention is to provide a sensitive test system which is capable of detecting minute amounts of retroviral RT in body liquids from humans or animals, cell samples or samples from virus propagation cultures, said system also being constructed so as to minimize the effects of the disturbing factors which are present in the above mentioned types of samples.

A still further object of the invention is to provide a method for eliminating the effect of the cellular polymerases, e.g. gamma polymerase, which may cause unsuitably high background activity in sensitive RT tests.

A still further object of the invention is to detect other nucleotide polymerising enzymes which are characterized by high processivity, which is used according to the invention.

The above and other objects of the invention will be explained in more detail in the following description of the determination method and its applications according to the invention.

The invention thus provides an improved analysis system for certain nucleotide polymerising enzymes. It is characterized by 1) using, in an initial capture step, a monoclonal antibody which is immobilized on a solid phase and is capable of binding at least one enzyme without detrimentally effecting the enzyme activity,
2) removing impurities and disturbing factors in a subsequent step, preferably by washing them away,
3) starting the reaction by adding a reaction solution which contains a primer/template construct, nucleotide substrate and preferably essential salts and co-factors, the reaction conditions being choosen so as to favour permanent association between the antibody-enzyme- and primer/template-constructs,
4) if necessary washing away untreated nucleotide substrate, primer/template and reaction solution and
5) determining, in a manner which is known per se, the amount of nucleotides which have been incorporated into the newly synthesised polymer.

This determination can e.g. be carried out by radiactive labelling, in which case the measurement can take place directly, or e.g. have the form of different types of modified bases, in which case the determination can be done by secondary reactions.

The key feature of the invention is step 3. Provided that suitable reaction conditions are used, the enzymes will bind strongly to the primer/template construct and the new labelled strand which is produced will remain bound to the immobilized enzyme. This makes it possible to separate substrate from product using a simple washing step, as mentioned above.

SHORT DESCRIPTION OF THE DRAWINGS

FIG. 1 shows the amount of RT activity which has been recovered on Mab beads as a function of absorption time and temperature.

SUMMARY OF THE TESTS ILLUSTRATED IN THE DRAWINGS

The results according to FIG. 1 were obtained by incubating HIV 1 RT ($2,7 \times 10^{-15}$ moles) at 8° C. (□) or at 20° C. (■) with Mab H2 bound to beads. The binding buffer was removed from the Mab beads at the indicated times and the distribution of RT between Mab beads and binding buffer was determined.

A) RT capture test: The Mab beads were washed and the RT activity which had been bound to the Mab beads was determined by an RT reaction for 2 h using $1,5 \times 10^{-7}$M of 3H-TTP (60 Ci/mmoles) as dNTP substrate. The reported data relate to cpm which have actually been recovered on each bead.

B) Soluble RT test (prior art): Remaining RT activity in the binding buffer was determined at the indicated times using a conventional RT test with $1,5 \times 10^{-7}$M of 3H-TTP (60 Ci/mmoles) as dNTP substrate. The RT activity was recalculated as procentage of a control consisting of RT in binding buffer which had been stored at 8° C. without any addition of Mab beads.

In the test which is illustrated in FIG. 2 HIV-1 RT ($1,8\times10^{-15}$ moles/sample) was incubated with Mab H2-beads for 3 h at 20° C. The Mab beads were then washed and reaction solutions were added which contained $1,5\times10^{-7}$ M of 3H-TPP (78 Ci/mmoles) and varying concentrations of prA$_{300}$ and odT$_{20}$. The reaction solutions were incubated at 33° C. and samples were taken after 2 (■), 4 (□) and 16 (♦) h respectively.

A) The amount of reaction product which had been recovered from the reaction solutions containing 20 mg of prA/ml and the indicated amount of odT$_{20}$.

B) The amount of reaction product which had been recovered from reaction solutions containing the indicated prA concentration when using a constant relation for prA/odT of 100/1.

The results which are shown in FIG. 3 relate to series dilution of HIV-1 RT from $2.5\times10^{-16}$ to $2.6\times10^{-13}$ moles of enzyme per sample, incubated with Mab H2 beads for 3 h at 20° C. The MAB beads were washed and a reaction solution containing $1.5\times10^{-7}$M of 3H-TPP (78 Ci/mmoles) was added. The reaction solutions were incubated at 33° C. and samples were taken out at the indicated time.

A) Symbols (moles of enzyme per sample): $2.5\times10^{-16}$ (□), $1.0\times10^{-15}$ (♦), $4.0\times10^{-15}$ (◇), $1.6\times10^{-14}$ (Δ), $6.4\times10^{-14}$ (▲) and $2.6\times10^{-13}$ (●).

B) Symbols (time in hours): 2 (■), 4 (□), 16 (♦) and 32 (◇).

Figure 4:
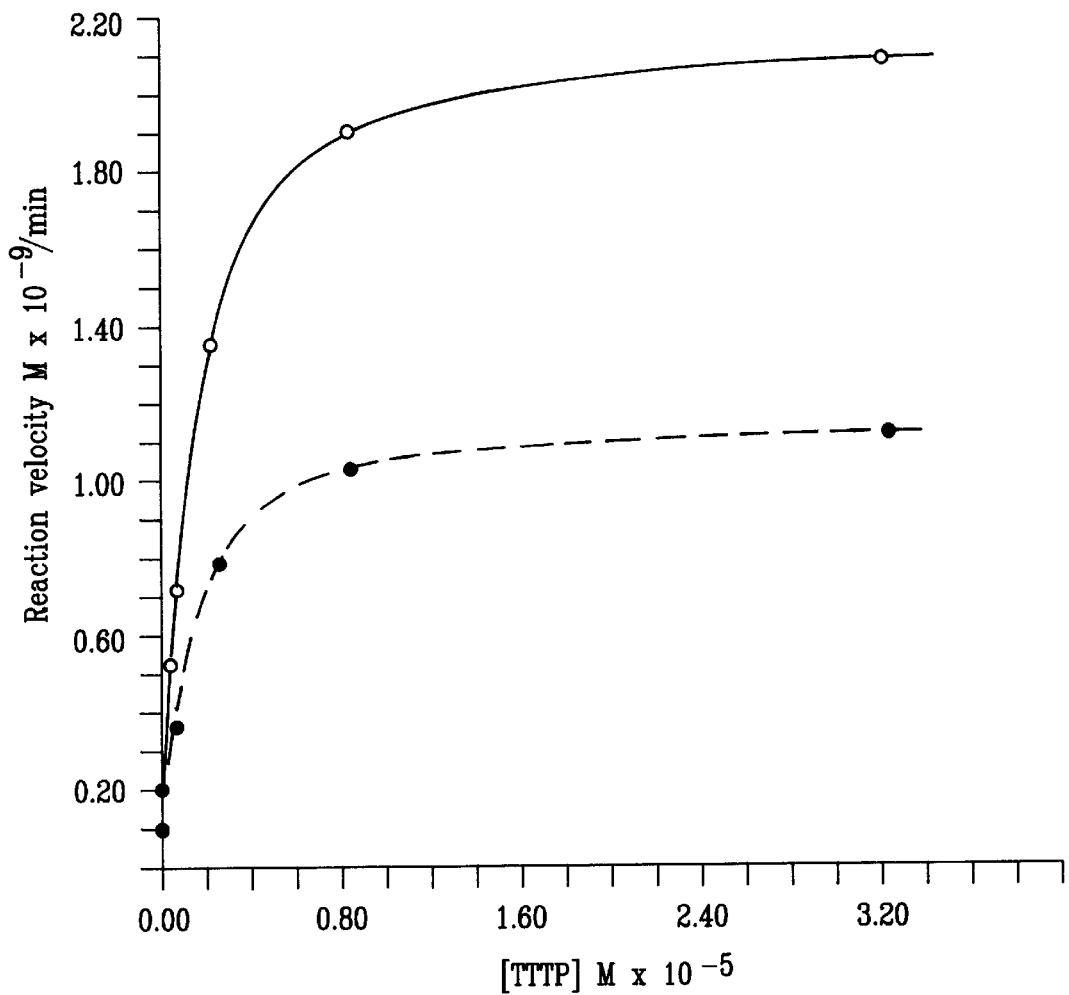
FIG. 4 shows a comparison between the substrate kinetics for free and immobilized HIV 1 RT respectively.

FIG. 4 shows initial reaction velocities at varying substrate concentrations for HIV-1 RT which has been bound to Mab H2 beads (●) and for free HIV-1 RT (○). The values have been obtained by measuring the reaction velocity for three different amounts of enzyme ($1.28\times10^{-14}$ moles/sample, $2.56\times16^{-4}$ moles/sample and $4.52\times10^{-14}$ moles/sample) and five different substrate concentrations (from $1.1\times10^{-7}$M to $3.2\times10^{-5}$M) using the capture test and the conventional RT test respectively. The test data obtained have been recalculated to the same amount of enzyme ($4.52\times10^{-4}$ moles/sample).

Figure 5:
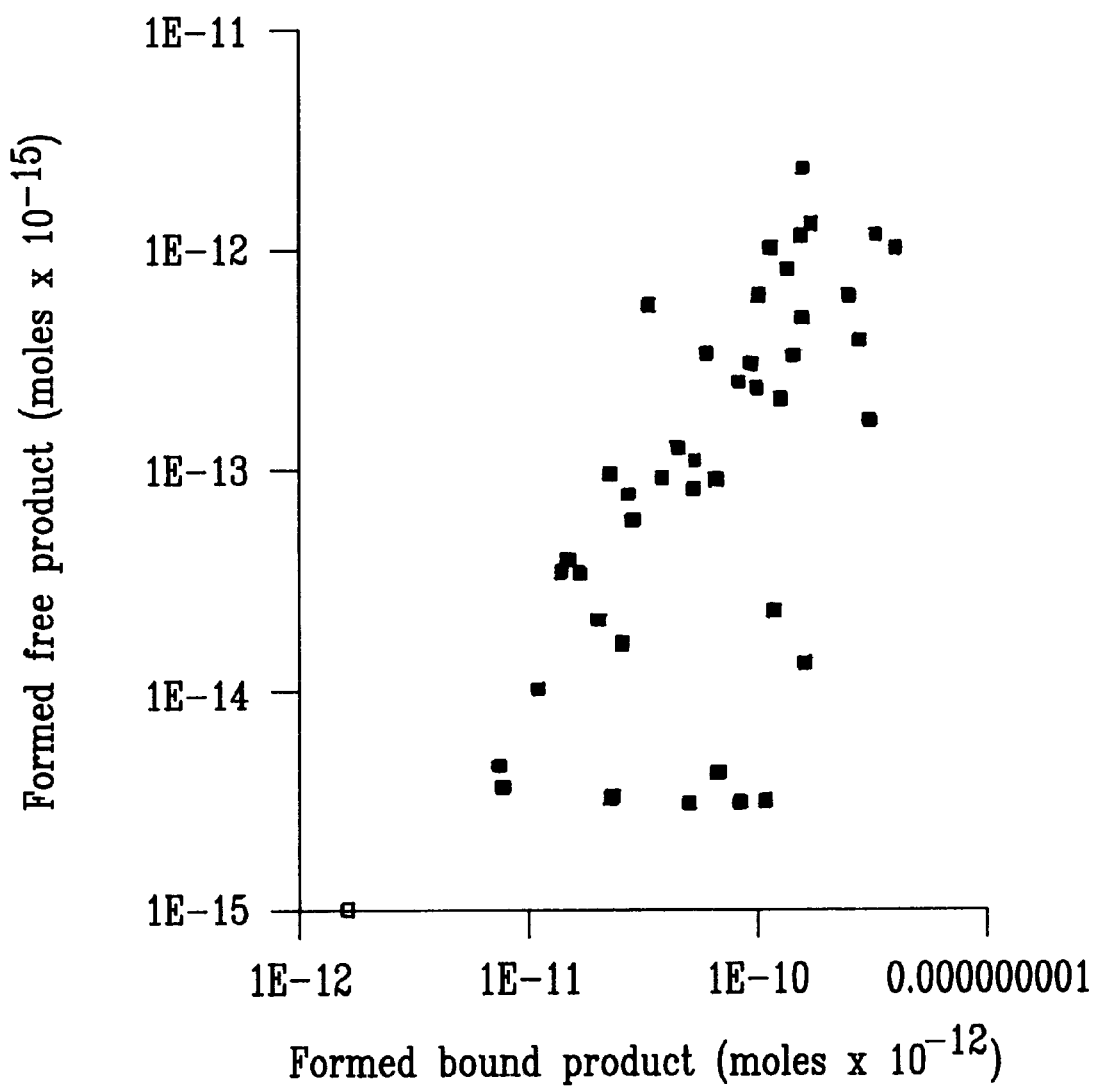
FIG. 5 is a diagram which shows the distribution of the RT reaction product between Mab H2 beads and reaction solution.

The diagram in FIG. 5 shows the distribution of labelled freshly produced DNA between Mab H$_2$ bead and the reaction solution after polymerisation reaction. The measurements have been carried out for three different enzyme concentrations (see FIG. 4) and five substrate concentrations (see FIG. 4). The samples which were taken after 2, 4 and 18 h respectively. Samples which did not give linearity in the RT capture test, due to depletion of the nucleoside substrate, were included in the analysis, whereas samples which did not provide significant detection (less than three times the background in the capture test) were excluded.

In the test which is illustrated in the diagram in FIG. 6, HIV-1 RT ($4.6\times10^{-15}$ moles/sample) were at first incubated with Mab H2 beads for 3 h at 20° C., unbound enzyme was removed by washing of the beads and the enzyme reaction was started by addition of a complete reaction solution containing $7.1\times10^{-7}$M of TTP (12.1 Ci/mmoles), prA (20 mg/ml) and odT (200 ng/ml). The amount of available A-bases on each bead, when all bound enzyme molecules bind one template (300 bases), corresponds to $8.2\times10^{-13}$ moles.

A) The first reaction solution, containing fee prA/odT, was removed from the beads after 2 h of incubation (at 33° C.) and was then replaced by new solutions containing 3H-TTP and the indicated additional components, prA/odT (♦), prA (■), odT (◇), non (□) and no prA/odT respectively between 2 and 4 h, and prA/odT was added after 4 h of incubation (▲). The samples were taken out at the indicated time and were re-calculated to the number of moles of TMP which had been incorporated in to DNA.

B) The first reaction solution was removed from the beads after incubation for 1 h and was replaced by new reaction solutions containing prA/odT and either unlabled TTP (□, ■) or $1.8\times10^{-5}$M ddtt (◇, ♦) as trinucleoside substrate. These reaction solutions were removed after incubation for another 2 h (not shown on the x scale in the figure) and were replaced by new solutions containing 3H TTP and either prA (□, ◇) or odT/prA (■, ♦) in standard concentrations. The samples were taken at the indicated times and were recalculated into the number of moles of TMP that had been incorporated.

Figure 7:
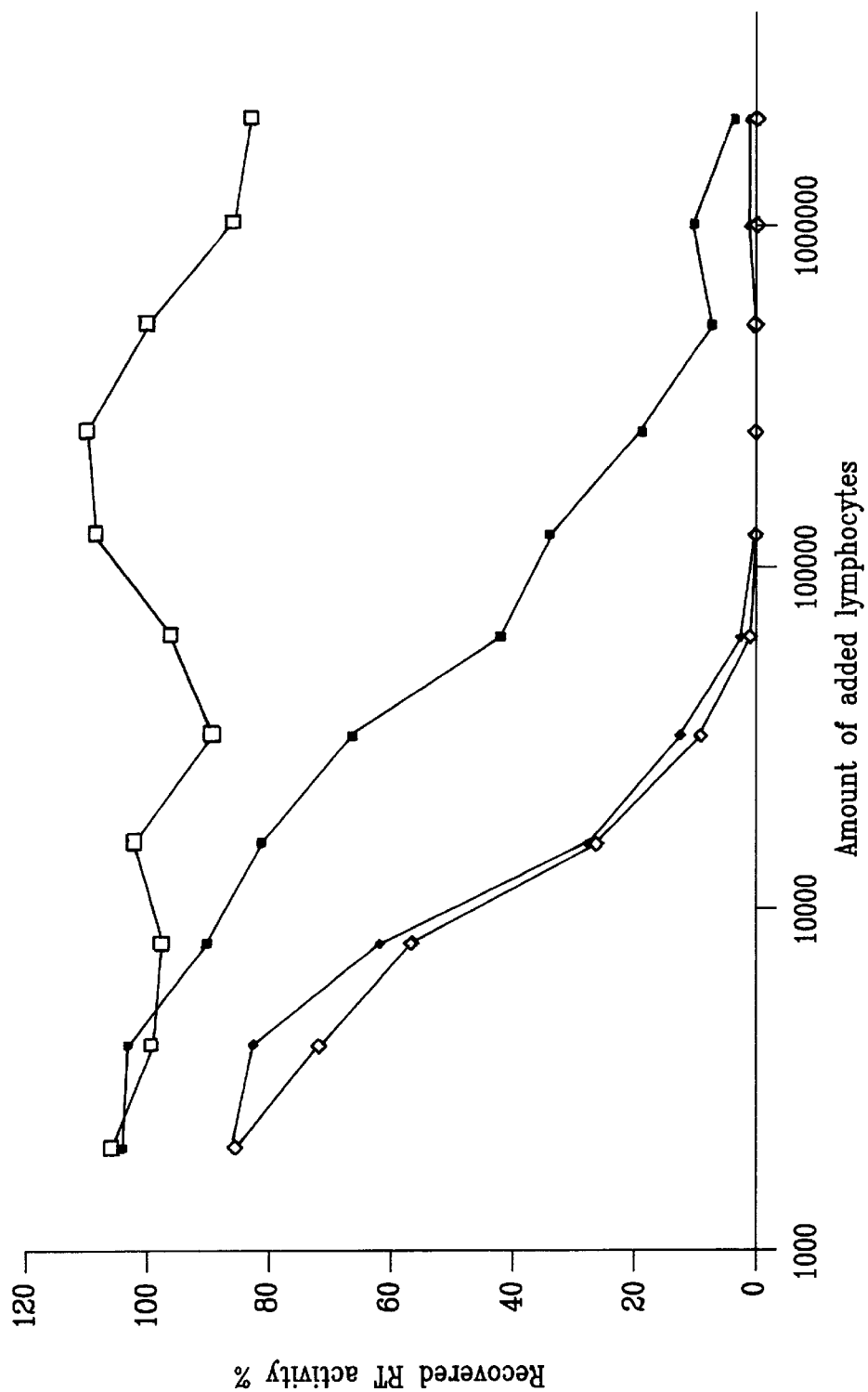
FIG. 7 is a comparison between the effects of lymphocyte extract on RT capture test and soluble test respectively.

The results which are reported in the diagram in FIG. 7 were obtained by mixing of recombinant HIV-1 RT ($2.5\times10^{-14}$ moles/sample) with the indicated amount of extract from peripheral blood lymphocytes and the RT activity in each sample was determined by RT capture test and soluble RT test respectively. The symbols have the following meanings: standard capture test (■), capture test with 2 mM phenylmethyl-sulphonylchloride (PMSF) and 20 g of prA included during the enzyme binding step (□), soluble standard test (◇), soluble test with 2 mM of PMSF added to the reaction solution (♦).

Figure 8:
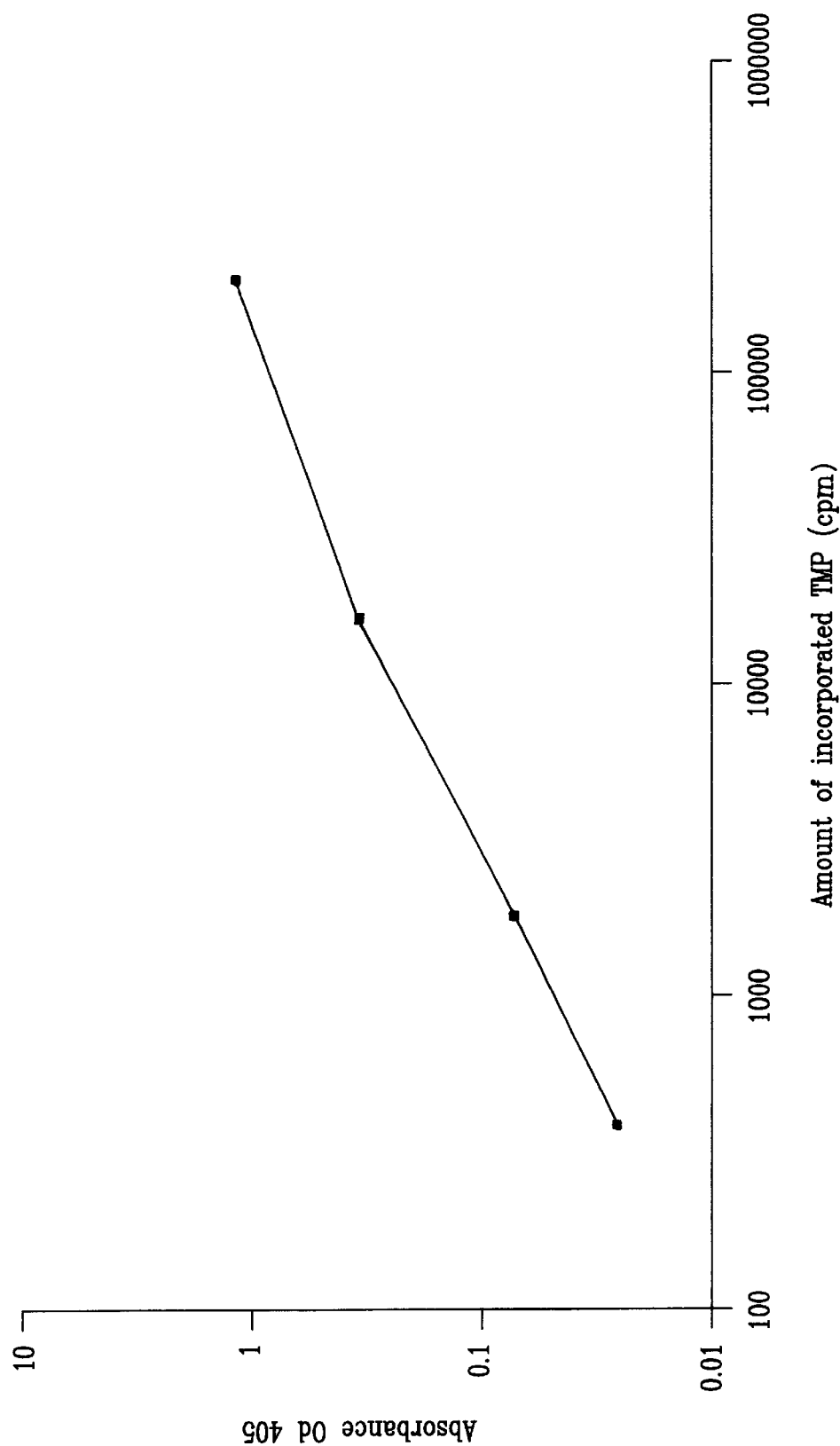
FIG. 8 is a diagram which compares two product detection systems in the RT capture test.
Figure 9A:
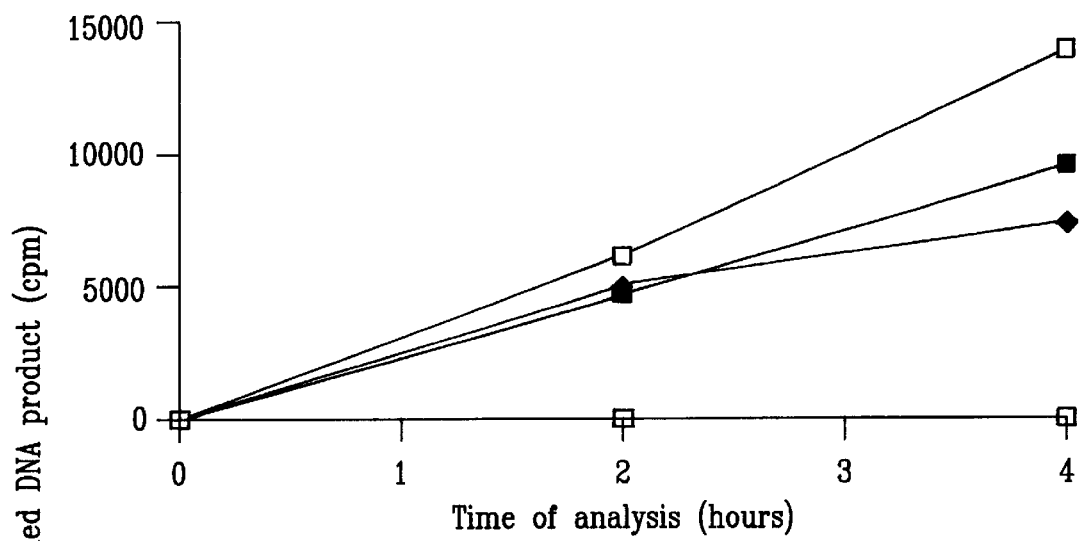
FIG. 9 shows the use of a capture test for measuring Herpes Simplex type I DNA polymerase, the various symbols representing four different Mab.
Figure 9B:
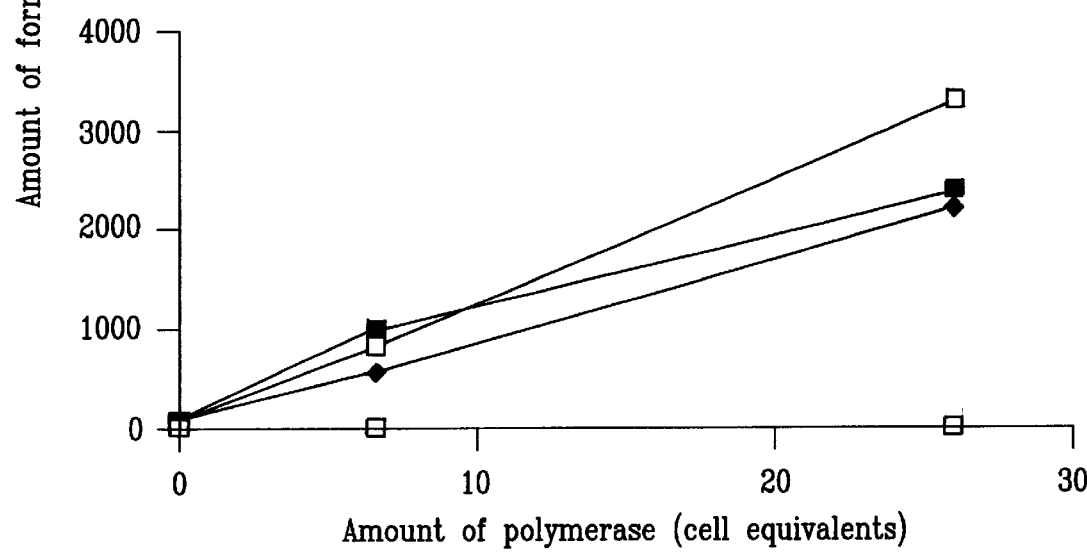

FIG. 8 shows how three dilutions of HIV-1 RT ($6.4\times10^{-16}$ moles/sample, $6.4\times10^{-15}$ moles/sample and $6.4\times10^{-14}$ moles/sample) were incubated with mab H2 beads for 3 h at 20° C. The amount of RT which was bound for each enzym dilution was determined by the use of two RT test systems. One of them was a standard test with $1.5\times3^{-7}$M of 3H-TTP as nucleoside substrate and direct detection of incorporated 3H-TMP. The second test was carried out using BrdUTP as nucleoside substrate and immunological detection of the reaction product. In both cases an incubation period of 150 minutes at 33° C. was used for the polymerization step. Incubation at 20° C. for 50 minutes was used for the Ap reaction.

SUMMARY OF THE TESTS REPORTED IN THE TABLES

Table 1. Characterization and Selection of Mab for the RT Capture test

Beads with immobilized monoclonals were incubated at 20° C. for 2 h with recombinant HIV-1 RT in binding buffer −/+0.5 M KCl. The amount of captured RT on Mab beads is reported as $^3$H-TMP which have been incorporated in bound and free nucleic acids respectively. Remaining RT activity in binding buffer without salt was determined by using a soluble RT test and was recalculated to % of a control consisting of HIV-1 RT which had been incubated with the non-HIV beads. The capability of each monoclonal to inhibit RT activity was checked in a separate test. Each ascites fluid was incubated with recombinant HIV-1 RT. Remaining RT activity was determined by the use of soluble RT test and recalculated to % of HIV-1 RT which had been incorporated with non-HIV ascites.

Table 2. The Linearity with Time in the Presence of Cell Extracts

The indicated amounts of recombinant HIV-1 RT were mixed with different amounts of an extract from peripheral blood lymphocytes. The recovery of RT activity was determined by means of the RT capture test and the correlation coefficients between the amount of product formed and the time of test was calculated. The amount of formed product was also re-calculated into % of the recovery from a control containing the corresponding amount of RT but no cell extract.

Table 3. The Linearity with the Amount of Enzyme in the Presence of Cell Extract A set of seven different 4-fold dilutions of recombinant HIV-1 RT (from $7.81 \times 10^{-17}$ to $8.00 \times 10^{-14}$ moles/sample) were mixed with an extract from $1.00 \times 10^{-6}$ peripheral blood lymphocytes (PBL). The recovery of RT activity was determined by means of the RT capture test and correlation coefficients between the amount of used enzyme and the amount of formed product was calculated directly from the cpm values obtained. For the used minimum, median and maximum concentrations of the enzymes the product recovery was also re-calculated into % of the recovery of a control which contained a corresponding amount of RT but no cell extract.

Table 4. The Capability of the Capture Test to Recover HIV-1 RT from Various Types of Samples Various components such as anticoagulants, Ficol, a protease inhibitor (PMSF) and cell extract were added to the binding buffer. The concentrations of the anticoagulants were those which are used for routine plasma sampling. The concentration of Ficol was 50% of the total binding buffer, and 2 mM of PMSF and 20 $\mu$g of prA were used as protecting agents. The beads were incubated for 3 h at 33° C. with HIV-1 RT and the various components were washed and the recovered RT activity was determined in a 2.5 h test. The data obtained were recalculated as % of an identically treated control, without any additives to the binding buffer. The upper part of the table shows the effect of the indicated components in the absence or presence of extracts from washed whole blood cells which had been isolated from citrate blood and re-suspended in binding buffer to half of the concentration in the original blood. The lower part shows the effects of including the indicated type of cell extract in the binding buffer.

WORKING EXAMPLES

The herein described RT capture test makes it possible to directly measure or detect RT also in impure samples and simplifies the final separation of substrate and product. The test comprises three main steps: first immunoaffinity purification of RT, then polymerization reaction and finally separation of substrate and product.

Selection of RT Binding Monoclonals and Binding Conditions for the Immunopurification Step The well known problems with measurement of DNA polymerizing enzymes in impure biological samples are the starting point for the problems which the present invention are intended to solve. The original idea was to construct a system for removing HIV RT from any unfavourable invironment by capturing the enzyme with use of an immobilized antibody against the enzyme. Disturbing factors such as RNA-ses, DNA-ses, nucleotidases, proteases and competitive template/primers could then be removed simply by a simple wash of the antibody-carrier. The optimal antibodies for this purpose should have the ability to rapidly capture RT in crude samples from all known HIV-1 isolates. They should also be capable filling this function without deter-mentaly effecting the polymerizing activity of RT. Several research teams have produced panels of monoclonals against HIV RT (Örvell et al. 1989, Restle et al. 1992, Szilway et al. 1992). A set of 18 mab were screened regarding the ability of rapidly capturing RT from HIV-1 in crude samples and interference with the activity of the captured RT enzyme. The various Mab clones were reactive with seven different epitopes of the HIV-1 RT protein (Table 1, column II).

the total recovery of radioactive reaction product in the capture test (Table 1, columns IV-VII) is a function both of the binding efficiency of the indicated Mab and the final activity of the bound enzyme. The capability of each Mab to capture RT can be seen from Table 1, column III, which shows remaining unbound RT activity in the binding buffer after incubation with the various Mab beads. The effect of the binding of each free Mab to HIV 1 RT in solution was evaluated in a separate RT inhibition test (Table 1: VIII). The Mab bead against the epitope 1, 4, 5 and 6 did not bind RT in a satisfactory manner. Mab beads against epitope 3 could bind RT, but the bound enzyme did not have the ability to efficiently synthesize DNA product due to partial inhibition of the RT activity (Table 1: VIII). Two Mab against two different parts of HIV 1 RT, H2 against p51 and Q7 against p15 (Örvell et al. 1989) were found be suitable for our purpose and were selected for further studies. These Mab were also found to be non-competitive and provided an additative effect in the capture test. A combination of H2 and Q7 on each bead was used for analysis of clinical material.

The proportion of RT which was recovered on the Mab beads was also dependent on the absorption time and temperature which was used in the binding step, as can be seen in FIG. 1. RT was incubated with the Mab H2 bead for the indicated time and at two different temperatures. The amount of RT activity on the bead increased with the incubation time, resulting in a proportional reduction of the remaining unbound RT activity in the binding buffer (FIG. 1).

Figure 2A:
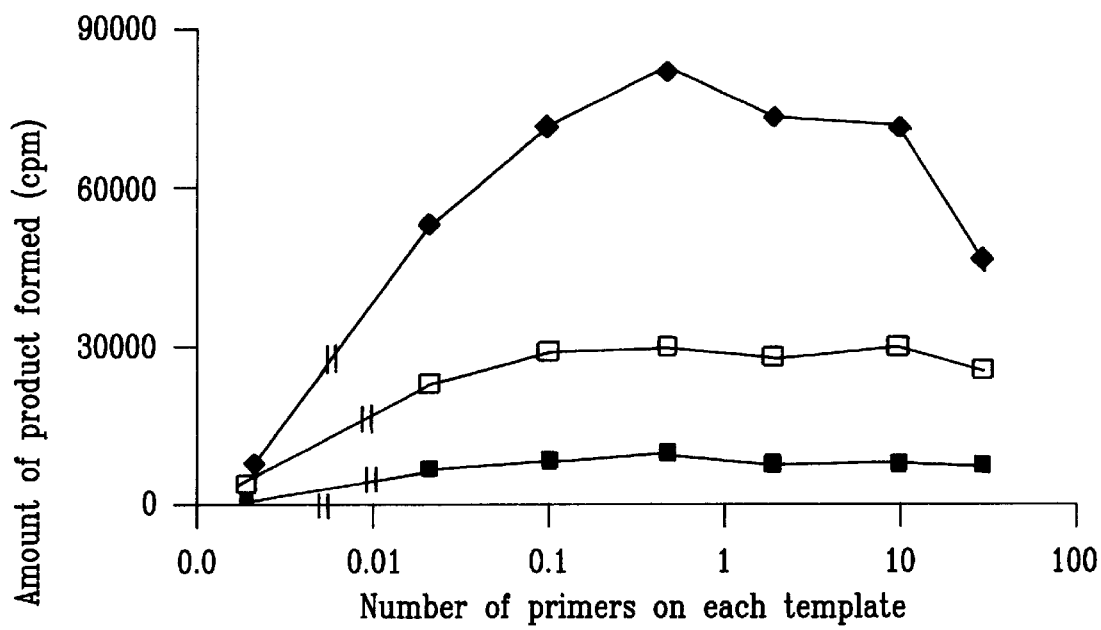
FIG. 2 is a diagram which shows the template/primer dependence (prA/odT) for optimal RT activity and linearity in time.

The Polymerization Reaction's Dependence of Primer and Template in the Capture Test The relation between odT primer concentration, reaction velocity and linearity in time on Mab H2 beads is exemplified in FIG. 2A. The primer requirement showed a rather wide optimum and the reaction velocity reached a maximum at 10–1000 ng odT/ml which corrresponds to 0.1–10 odT 20 primers/-template. Use of smaller amounts of primer resulted in reduced reaction velocity and also poor linearity vs time. If the reaction solution completele lacked primer there was only formed an insignificantly detectable reaction (FIG. 2A).

Figure 2B:
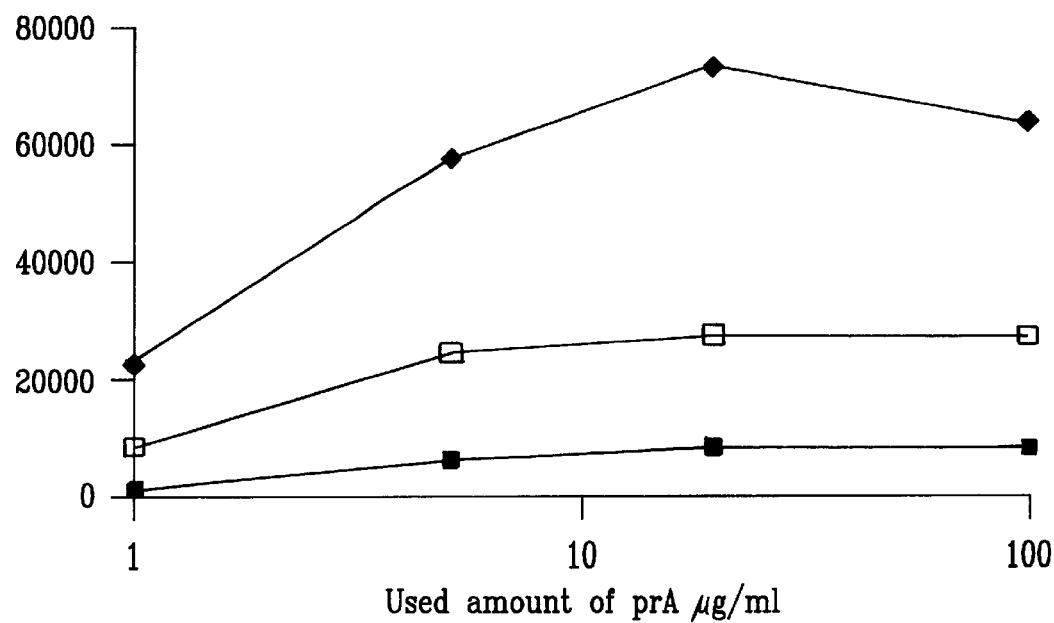

The reaction velocity as a function of the template concentration at a constant prA/odT relation of 100:1 is shown in FIG. 2B. A saturated system in which the template concentration did not limit the reaction velocity and linearity with time was reached when using at least 20 mg prA/ml, corresponding to $1.08 \times 10^{-8}$ moles of A bases/tube. The combination of 20 mg/ml of prA and 0.2 mg/ml of odT20 showed to be suitable as standard conditions for our RT capture test.

Figure 3A:
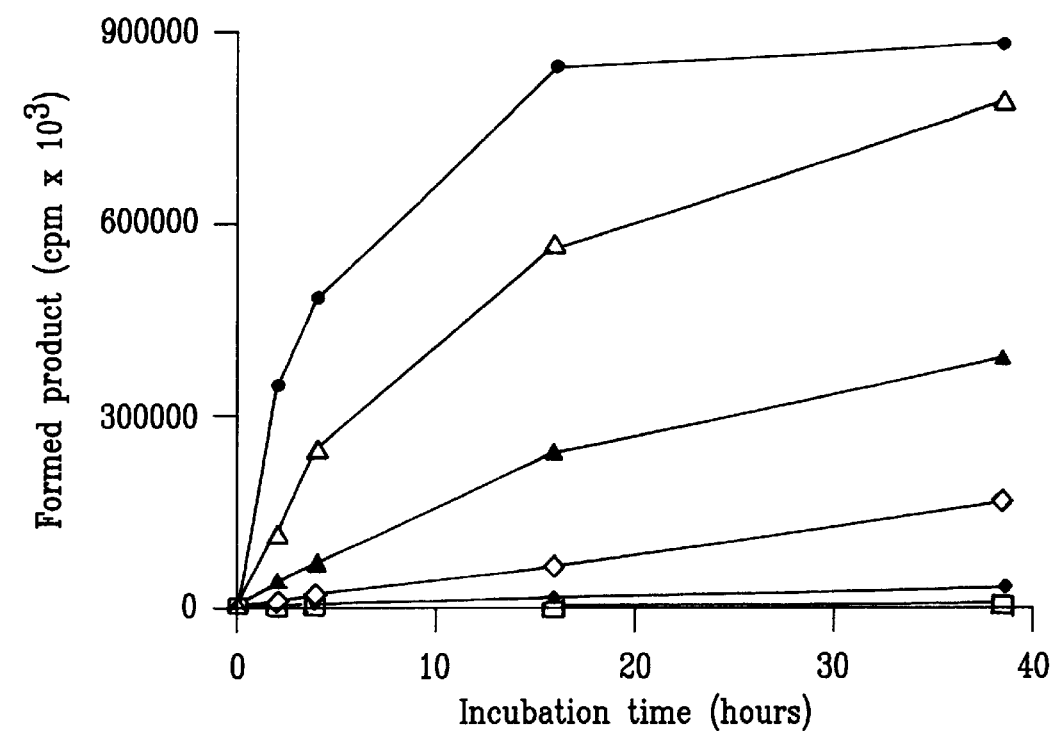
FIG. 3 shows the linearity with time and the amount of enzyme for the RT capture test.
Figure 3B:
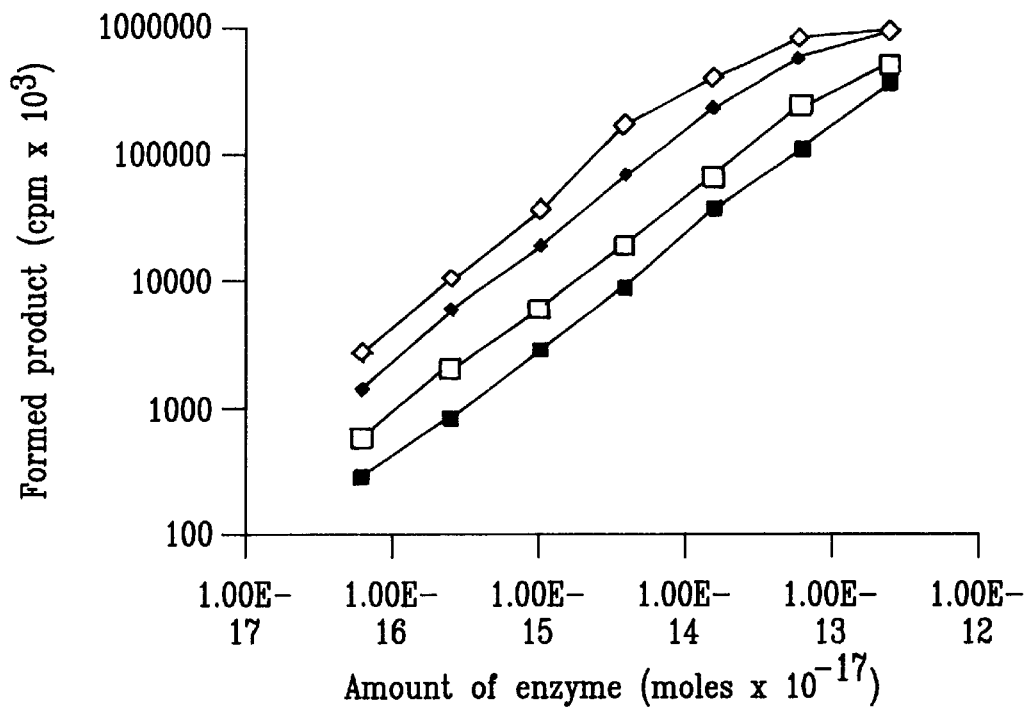

Evaluation of the Enzymatic Properties of the Immobilized HIV 1 RT in the Capture Test The relation between the amount of formed product and the reaction time for RT is illustrated in FIG. 3A. The enzyme reaction was linear at least up to 16 h as long as not more than $1.6\times10^{-14}$ moles of HIV 1 RT was used in each test. Higher enzyme concentrations result in substrate depletion, thereby shortening the time for linear enzyme reaction. When using an analysis time which is shorter than 4 and using $1.5\times10^{-7}$ M of 3H-TTP (80 Ci/mmoles) as substrate, a linear relation is observed between incorporated marker and amount of enzyme, up to $6.4\times10^{-14}$ moles of HIV 1 RT in each test (FIG. 3B). FIG. 4 shows a Menten diagram which illustrates the nucleotide substrate kinetics for free and immobilized HIV 1 RT. The initial reaction velocities for five concentrations of TTP, from $1.1\times10^{-7}$ to $3.2\times10^{-5}$, were determined by means of a conventional soluble RT test and with the RT capture test according to the invention, identical reaction conditions being used. Free HIV 1 RT in soluble test resulted in a Km value of $1.21\times10^{-6}$ M, which can be compared with $1.18\times10^{-6}$M for HIV 1 RT which has been immobilized on mab 2 beads. When the reaction velocities are recalculated into equal amounts of RT added to both test systems ($4.52\times10^{-14}$ moles/sample, FIG. 7), free and immobilized enzyme had Vsat values of $2.04\times10^{-9}$ and $1.18\times10^{-9}$ M/min respectively, i.e. The Vsat value seems to be about 40% lower for the immobilized enzyme. It should, however, be kept in mind that the comparison of the reaction velocities according to FIG. 4 is based on addition of equal amounts of RT in each test. The binding of RT to immobilized H2-mab is a time and temperature dependent reaction. As appears from the diagram in FIG. 2, about 40% of total RT which has been added to the sample will remain in solution under the binding conditions which are described in connection with FIG. 6 (0.5 M KCl, 20° C. and an incubation time of 3 h). The nucleoside substrate kinetics will obviously not be essentially changed by the immobilizaiton of the enzyme. This means that the RT capture test according to the invention can be used for characterization of possible antiviral substances.

Separation of Substrate and Product in the RT Capture Test

IN the last step of the RT capture test remaining TTP substrate from TMP, which has been incorporated into the DNA product, will be separated by a simple wash of the carrier bead. Not only the substrate but also all DNA product which has been released from the immobilized enzyme during the reaction will then not be detected. The effect of these factors on the product recovery was determined by analysis of the distribution of the RT reaction product between Mab H2 beads and the reaction solution within a broad range of products amounts, as illustrated in FIG. 5.

As can be seen from this Figure, theses variables were correlated (r=0.46, m=45, p<0.005). Incrasing the amount of bound product resulted in an increased amount in the free product. The found relation between free and bound reaction product was between $2\times10^{-6}$ and $1.7\times10^{-2}$ (median value $2.3\times10^{-3}$). However, the amount of free labled nucleic acid was never greater than 1.7% of bound nucleic acid, in spite more than 250 fold variation of the amount of product formed.

Processive DNA Synthesis over Template Boarders in the RT Capture Test

One of the more surprising properties of the enzyme test according to the invention is that virtually all product from the enzyme reaction is recovered as immobilized enzyme/ product complex. Release of the template from the immobilized enzyme obviously a very rare occation once the elongation reaction has started. When starting on a primed, about 300 A bases long template, the RT capture test according to the invention is capable of providing a linear incorporation of 3H-TTP for at least 32 h. A calculation of the total amount of the immobilized T strands which are produced for 16 h using $4.6\times10^{-15}$ moles of HIV 1 RT/sample, provides about 11,000 bases. It is true that the processivity of HIV-1 RT on prA templates is unusually high (Majumdar et al. 1988, Huber et al. 1989), but the product is more than 30 times longer than the template used.

In the test illustrated in FIG. 6 there is at first created an immobilized enzyme-primer/template-complex under 3 hours of incubation at 20° C. The effect of the addition of reaction components is then evaluated for a second incubation period. The amount of incorporated TMP product per molecule of bound enzyme was in long term tests (16 h) for the reactions with excess of prA found to exceed the amount which is possible to incorporate in a single template (300 A bases), more than 30 fold. Removable of the template from the reaction solution reduced the reaction velocity dramatically, whereas addition of a new template restored the velocity (FIG. 7A). The enzyme reaciton obviously uses free A strands as templates for the growing, immobilized pdT strand. A possible explanation of these observations is that the reaction starts from the initial primer, proceeds along the first template stretch to the template limit. The end of a new prA template is then incorporated into the growing hybride and the enzyme reaction will continue. This sequence will then be repeated for the next template-boarder and so on "eternally".

A confirmation of this idea is that it has been reported (Hubert et al. 1989) that HIV-1 RT is capable of forming long projecting single stranded DNA strands over the template boarders. The same scientists also have hinted that the enzyme remained bound to the end of the extended primer.

Figures 6A, 6B:
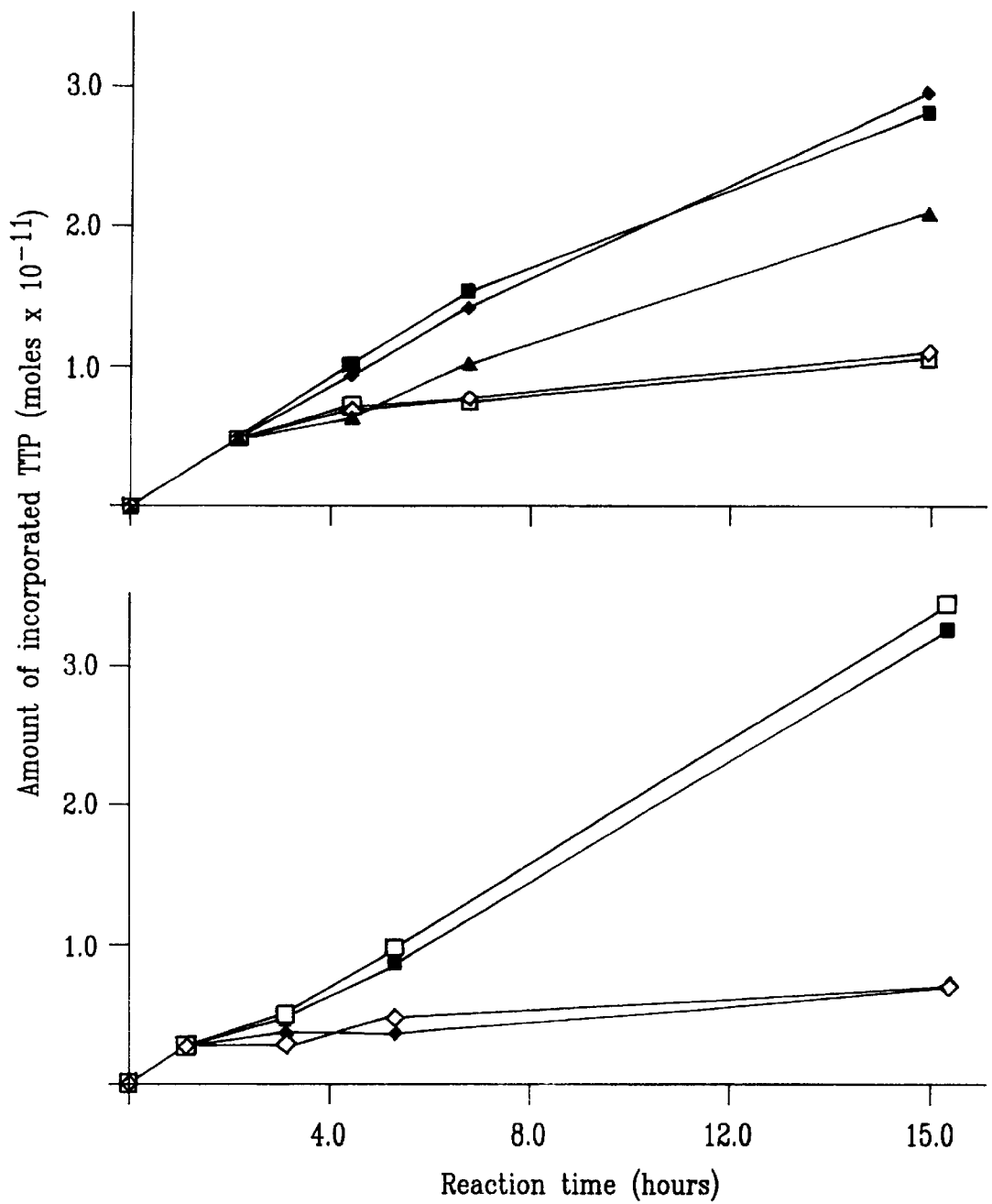
FIG. 6 is a diagram which illustrates processive DNA synthesis over template boarders in the RT capture test.

The capability of the immobilized enzyme to change primer was investigated in a special test. An immobilized enzyme template/primer-complex was produced during a first incubation. This extended primer is made useless by a second incubation with $1.75\times10^{-5}$ M of ddTTP. The effect of addition of a new primer/template was then, after removal of excess of ddTTP, controlled by washing of the immobilized enzyme complex. The results showed that virgually all activity of the immobilized enzyme had disappeared and not could be restored by adding new prA or prA/odT (FIG. 6B).

Taken all together our data show unexpectadly high processivity for the RT enzyme. Separation of substrate and product is simple. Just wash the beads. This has made it possible by optimation of the analysis conditions in order to avoid dissociation of the enzyme-primer/template-complex. Important factors are the use of a prA template, low ion strength and incorporation of an RNas H inhibitor (e.g. dextrane sulphate) in the reaction solution.

Comparison Between the RT Capture Test and Soluble RT test in the Presence of Cell Extract Recombinant HIV-1 RT was mixed with the indicated amounts of an extract of peripheral blood lymphocytes and remaining RT activity was determined with the RT capture test according to the invention and soluble RT test respectively. The amount of cell extract which inhibited 50% of the RT activity corresponds to about 10,000 cells in the soluble test, to be compared with about 50,000 cells in the RT capture test (FIG. 7). An analysis of the inhibiting effects of the cell extract on the capture test revealed presence of proteolytic enzymes during the RT binding step. Incorporation of 2 mM phenyl-methylsulphonyl-fluoride (PMSF) and prA (20 g/ml) in the RT binding step eliminated most of the inhibiting effects of the cell extracts on the capture test. Addition of the same components to the reaciton mixture of the soluble test had no effect (FIG. 7).

As can be seen from Table 4 the RT capture test has a similar capability of recovering RT from other types of cell extracts. As regards ficol and different types of anticoagulants the table indicates that EDTA is not especially suitable for testing of blood cells with the RT capture test.

Table 2 shows the linearity with time in the presence of cell extract. From the table, which analyses the effect of a constant amount of HIV-1 RT, it can be seen that the product recovery is linear with time up to 14.5 h, provided that extract from no more than 500,000 PBL cells/sample are present. Addition of more cell extract resulted in reduced product recovery in long term test.

Immunological Determination of the Reaction Product

The analysis system according to the invention can be combined with different types of systems for product determination. FIG. 8 shows a comparison between our standard system for detection, with the use of radiolabelled nucleoside substrate and a colorimetric system based on Ap conjugated rat antibodies. As can be seen in FIG. 8 the relation was linear between the values in the two systems. This shows that the RT capture test easily can be adapted for colorimetric product detection. The detection sensibility in today's colorimetric systems is a function of the incubation time in the RT test step, but also of the time for the final Ap analysis. The Od405 values in FIG. 8 were obtained after 50 minutes of Ap reaciton. A stronger signal could be obtained when using a longer incubation time.

Capture Test for Herpes Simplex Type 1 DNA Polymerase

Five mouse-Mabs which were produced against herpes virus type 1 UL42 polymerase complex (Wilcock 1991) were immobilized on plastic beads using the same procedure as the one described above for anti-HIV-1 RT beads. Extracts from BHK21-13S cells infected with HSV 1 (strain C42) was produced according to known prior art (Gronowitz and Källander 1980).

The samples were diluted 1:1 in a buffer containing: 10 mM Tris, pH 7.6; $MgCl_2$, 4 mM; KCl, 0.15 M; Triton-X 100, 0.5%; and $NaN_3$, 0.05 mg/ml. In the first analysis step a set of tubes containing a polystyrene bead with immobilized anti UL42 MAb and 200 $\mu$l sample dilution tube, at 33° C. for 1.5 h to let MAb bind to the UL42 polymerase complex. The beads were then washed four times with a buffer consisting of 3 mM Tris, pH 7.6 and 0.1% of Triton-X 100 for removing disturbing factors coming from the samples. In the next incubation step the polymerization reaction was started by adding 200 $\mu$l of a complete DNA polymerase reaction mixture per tube to the immobilized MAb-UL42 polymerase complex. The final concentrations for the non-speed restricted components were as follows: Tris-HCl, 10 mM, pH 7.6; $MgCl_2$, 4 mM; KCl, 200 mM; DTE 10 mM; Spermidine, 1 mM; Triton-X 100, 0.5%; GTP, 100 $\mu$M; bovine serum albumine, 0.5 mg/ml. $odT_{22}$ (1 $\mu$g/ml) was used as primer, $pdA_{300}$ (10 $\mu$g/ml) as template and $1.5 \times 10^{-7}$ M of $^3$H-dTTP (specific activity 40–80 ci/mmoles) as nucleotide substrate. The continued treatment of the beads was carried out as in the HIV RT capture test.

TABLE 1

| | | | Recovery of incorporated radioact. after RT capture test | | | | |
|---|---|---|---|---|---|---|---|
| | | Remain. RT act. after | Mab beads with: | | in free nucleic acids with: | | RT inhib. test |
| Clone<br>Column I | Epitope<br>No.*<br>II | bind to<br>Mab beads<br>(%)<br>III | No<br>salt<br>(cpm)<br>IV | KCl<br>(cpm)<br>V | No<br>salt<br>(Cpm)<br>VI | KCl<br>(cpm)<br>VII | remain.<br>activity<br>(%)<br>VIII |
| Non-HIV (a-urokinase) | — | 100 | 705 | 270 | 543 | 110 | 100 |
| A1 (940C6) | 1 | 103 | 1806 | 501 | 2480 | 106 | 78 |
| B1 (950C11) | 1 | 109 | 128 | 126 | 413 | 106 | 69 |
| C2 (1.148F2) | 2 | 85 | 26650 | 17509 | 683 | 973 | 60 |
| D2 (1.149B6) | 2 | 51 | 8893 | 54436 | 1200 | 2753 | 72 |
| E2 (1.150E2) | 2 | 52 | 30235 | 58691 | 2160 | 1303 | 112 |
| F2 (1.158E9) | 2 | 45 | 25546 | 35764 | 2983 | 2363 | 60 |
| G2 (1.158F7) | 2 | 89 | 14922 | 10708 | 4560 | 543 | 76 |
| H2 (1.166C2) | 2 | 57 | 44665 | 64770 | 2550 | 2696 | 90 |
| J3 (1.151F8) | 3 | 101 | 1122 | 282 | 1066 | 196 | 38 |
| K3 (1.152B3) | 3 | 55 | 20827 | 2759 | 1073 | 193 | 59 |
| L3 (1.158E2) | 3 | 88 | 3905 | 497 | 3636 | 376 | 36 |
| M3 (1.163C4) | 3 | 88 | 3560 | 2302 | 2536 | 476 | 17 |
| N4 (1.153G10) | 4 | 104 | 149 | 23 | 153 | 103 | 75 |
| O5 (996E5) | 5 | 94 | 80 | 63 | 1420 | 220 | 74 |
| P6 (1.009G9) | 6 | 93 | 3579 | 1001 | 3560 | 703 | 129 |
| Q7 (1.158E10) | 7 | 60 | 35591 | 37476 | 1810 | 1230 | 89 |
| R7 (1.160B3) | 7 | 62 | 28440 | 13199 | 2836 | 993 | 61 |
| S7 (1.162D10) | 7 | 70 | 26469 | 12210 | 1683 | 930 | 70 |
| H2 + Q7 | 2 + 7 | 45 | 71097 | 99309 | 1136 | 1456 | 101 |
| E2 + Q7 | 2 + 7 | 59 | 66193 | 75114 | 2350 | 2486 | 109 |
| H2 + R7 | 2 + 7 | 56 | 65562 | 72965 | 3256 | 1630 | 73 |
| H2 + S7 | 2 + 7 | 50 | 63654 | 79184 | 2303 | 1910 | ND |
| D2 + Q7 | 2 + 7 | 57 | 44525 | 70799 | 933 | 2176 | 76 |

*According to Örvell et al. 1989.

TABLE 2

Linearity with the time in the presence of cell extract

| Amount of RT enzyme moles/ samples | Amount of PBL extract cells/ sample | Product recovery at indicated time, % of a control without extract | | | Correl. coeff. between the amount of formed product and test time | |
|---|---|---|---|---|---|---|
| | | 2.5 h | 14.5 h | 38.5 h | Sample | Control |
| $2.50 \times 10^{-14}$ | $2.00 \times 10^{6}$ | 84% | 49% | ND | 0.972 | 0.992 |
| $2.50 \times 10^{-14}$ | $1.00 \times 10^{6}$ | 86 | 63 | ND | 0.984 | 0.992 |
| $2.50 \times 10^{-14}$ | $5.00 \times 10^{5}$ | 100 | 100 | ND | 0.995 | 0.992 |
| $2.50 \times 10^{-14}$ | $2.50 \times 10^{5}$ | 110 | 97 | ND | 0.996 | 0.992 |
| $2.50 \times 10^{-14}$ | $1.25 \times 10^{5}$ | 108 | 105 | ND | 0.998 | 0.992 |

TABLE 3

| Test time | Product recovery at indicated amount HIV in each sample (% of cell free control) | | | Corr. coeff.* between enzyme and amount of product | |
|---|---|---|---|---|---|
| | $7.81 \times 10^{-17}$ | $5.00 \times 10^{-5}$ | $8.00 \times 10^{-14}$ | sample | control |
| 2 | 108 | 74 | 65 | 0.976 | 0.991 |
| 4 | 80 | 70 | 86 | 0.991 | 0.968 |
| 16 | 57 | 51 | 86 | 0.998 | 0.910 |
| 38 | 14 | 17 | 65 | 0.994 | 0.810 |

*Calculated from seven observations

TABLE 4

| | RT activity after addition of indicated component to binding buffer, recalculated as % of control without additive | | |
|---|---|---|---|
| | None | Blood cells | Blood cells, PMSF, prA |
| Component in binding buffer | | | |
| RT | 100 | 15 | 45 |
| RT + PMSF + prA | 98 | — | 45 |
| RT + EDTA | 96 | 19 | 40 |
| RT + citrate | 68 | 28 | 97 |
| RT + heparine | 61 | 55 | 120 |
| RT + Ficol | 112 | 51 | 96 |
| Addition of indicated cell material | | | |
| blood cells (EDTA) | 100 | ND | 64 |
| $2 \times 10^{6}$ PBL (Ficol) | 100 | 5 | 82 |
| $1 \times 10^{6}$ PBL (Ficol) | 100 | 9 | 90 |
| $1 \times 10^{6}$ Activated PBL* | 100 | ND | 72 |

*Normal peripheral lympocytes which had been isolated with Ficol gradient centrifugation activated with PHA and used as negative control for HIV isolation.

The Ability of the RT Capture Test to Detect RT Activity in RT Infected Cell Cultures 18 blind coded cultures, which had been infected with 16 different HIV isolates representing a great variety of biological properties were analyzed after expression of RT and P24-antigen. The analyzed samples were taken out every two days and RT analysis was performed by addition of 100 μl of crude cell structure suspension to the capture test set, whereas 22.5 ml of supernatant was used in P24 ELISA. Data as reported in Table 4 shows almost perfect agreement between the results in the two tests. There was a strong correlation between the RT activity and the found amounts p24 (r=0.947, p<0.01, n=17) when the analysis was restricted to samples which gave significant values in both tests. All of the samples which were positive in the p24 test were also positive in the RT capture test, whereas 9 samples which were not significant or gave boarderline values in p24 ELISA, were positive in the capture test. This shows that tests had similar detection sensibility for the investigated isolates. When "the code was broken" after five days it was found that all HIV 1 isolates which had been designated "rapid high" in accordance with their behaviour during the isolation of tem, already had caused a notable RT activity. Five of the seven HIV isolates which had been designated "slow low", i.e. which on isolation grew slowly and give low titers, showed remarkable RT activity after 6 days of incubation. No activity could be detected in the uninfected control cultures or the two HIV-2 infected cultures.

What is claimed is:

1. A method for determining the activity of a DNA polymerizing enzyme in a sample where
   in an initial capture step the DNA polymerizing enzyme intended for determination is captured by means of a monoclonal antibody which is immobilized on a solid carrier and is capable of binding said DNA polymerizing enzyme without detrimentally affecting the DNA polymerizing enzyme activity,
   in a subsequent step contaminants and disturbing factors are removed,
   nucleotide polymerization for the formation of DNA is started by the addition of a reaction solution containing a primer, a template and a nucleotide substrate, comprising
      choosing reaction conditions for the polymerizing reaction to result in permanent association between the newly synthesized DNA polymer and the captured DNA polymerizing enzyme,
      optionally, washing away nucleotide substrate, primer, template and reaction solution from the DNA polymer obtained,
      determining the amount of nucleotide incorporated in said DNA polymer associated with the immobilized DNA polymerizing enzyme and through this determination of the amount of nucleotide determining the DNA polymerizing enzyme activity.

2. A method according to claim 1, wherein the enzyme intended for the determination is DNA polymerase.

3. A method according to claim 1 wherein the DNA polymerizing enzyme is reverse transcriptase.

4. A method according to claim 1, comprising the determination of incorporated nucleotide by radioactive marking of the nucleotide.

5. A method according to claim 2, comprising the determination of incorporated nucleotide by radioactive marking of the nucleotide.

6. A method according to claim 3, comprising the determination of incorporated nucleotide by radioactive marking of the nucleotide.

7. A method according to claim 1, comprising the determination of incorporated nucleotide by non-radioactive marking of the nucleotide.

8. A method according to claim 2, comprising the determination of incorporated nucleotide by non-radioactive marking of the nucleotide.

9. A method according to claim 3, comprising the determination of incorporated nucleotide by non-radioactive marking of the nucleotide.

10. A method according to claim 1, comprising the determination of incorporated nucleotide by colorimetric assay.

11. The method according to claim 1, for the determination of HIV1 RT activity in a sample.

12. The method according to claim 1, for the determination of Herpes Simplex DNA polymerase activity in a sample.

* * * * *